United States Patent [19]

Topping

[11] Patent Number: 5,268,632
[45] Date of Patent: Dec. 7, 1993

[54] ELECTRODE ASSEMBLY TEST UNIT AND METHOD

[75] Inventor: Joseph Topping, North Wales, Pa.

[73] Assignee: Henkel Corporation, Ambler, Pa.

[21] Appl. No.: 876,237

[22] Filed: Apr. 30, 1992

[51] Int. Cl.⁵ .................. G01N 27/00; G01N 27/26
[52] U.S. Cl. .................. 324/71.1; 204/401; 324/425
[58] Field of Search ............ 324/72, 71.1, 425, 73.1; 204/401, 406; 422/82.01, 82.02, 82.03

[56] References Cited

U.S. PATENT DOCUMENTS

| | | | |
|---|---|---|---|
| 3,966,413 | 6/1976 | Marinenko | 204/406 |
| 4,048,041 | 9/1977 | David et al. | 324/425 |
| 4,120,658 | 10/1978 | Bruttig | 422/82.03 |
| 4,124,475 | 11/1978 | Zetter et al. | 204/406 |
| 4,189,367 | 2/1980 | Connery et al. | 204/401 |
| 5,022,980 | 6/1991 | Tanaka et al. | 204/401 |
| 5,046,028 | 9/1991 | Bryan et al. | 204/401 |

Primary Examiner—Kenneth A. Wieder
Assistant Examiner—Maura K. Regan
Attorney, Agent, or Firm—Ernest G. Szoke; Wayne C. Jaeschke; Kenneth Watov

[57] ABSTRACT

A test unit for a monitoring device includes reference and measuring electrodes coupled to a preamplifier and a temperature compensating resistor for the preamplifier. The test unit has components corresponding to those of the monitoring device as well as a power supply and a voltmeter coupled to the output of its preamplifier. Cables are provided for substituting either or both electrodes of the monitoring device for the electrodes of the test device, and a switch is provided for substituting a temperature compensation resistor of the monitoring device for the temperature compensation resistor of the test device. A cable is adapted for connection to either preamplifier for supplying it with operating potentials derived from the power supply and for coupling the output of either preamplifier to the voltmeter.

19 Claims, 5 Drawing Sheets

ELECTRODE ASSEMBLY TEST UNIT AND METHOD

BACKGROUND

1. Field of the Invention

The field of technology of the present invention relates generally to measurement systems, and more specifically to test units for testing components of chemical activity measurement devices.

2. Discussion of Related Art

There are a considerable number of processes involving the use of chemical solutions where it is essential that the solution have a given concentration of ions. By way of example, when corrosion resistent coatings are formed on aluminum with compounds of fluorine it is important to have a given concentration of active fluoride, i.e., fluoride ions. When a single aluminum structure is to be coated, the amount of active fluoride can be determined from the molar concentration of fluorine. However, when successive coatings of uniform color and appearance are to be formed, it is necessary to replenish the solution in such a way as to maintain a consistent level of fluoride ion activity regardless of the molar concentration of fluorine.

Fluoride ion concentration can be determined by finding the rate at which the solution etches soda lime glass. The glass is weighed, and after it is exposed to the solution for a given time interval at a carefully controlled temperature, the products formed by the etching process are washed away and the glass is weighed again. The loss in weight of the glass divided by the time interval gives the desired etching rate that is proportional to the concentration of fluoride ions. But, since the time required for an accurate measurement may take several days, this method is impractical for continuous production processes.

In order to obtain an instantaneous indication of the fluoride ion concentration, a monitoring device is immersed in the solution. It is comprised of a reference electrode, a lanthanium fluoride ion selective electrode and a preamplifier for amplifying the voltage between the electrodes. In order that the gain of the amplifier remain constant in the presence of temperature changes, a temperature compensation resistor is coupled to it. The output voltage of the amplifier is transmitted to a remote control station where it is used to control the addition of chemicals to the solution so as to maintain a desired fluoride concentration. Because the corrosive effect of the solution on the components, they have to be checked from time to time to ensure that they meet specifications required for proper operation.

A straight forward way to check the components is to physically substitute them for components in an on-line monitoring device that is known to operate properly, but experience has shown that the components are often damaged so that a good component is destroyed. Unfortunately, this is especially true of the expensive measuring electrode.

A similar situation is encountered with monitoring devices for the pH value of solution used in cleaning processes.

3. Summary of the Invention

In accordance with this invention, a portable test unit is provided having components like those of the monitoring device and a voltmeter for indicating the output of its preamplifier. The test unit permits components of the monitoring device to be tested remotely from the site where the monitoring device is used. Provision is made for electrically substituting the components of a monitoring device for those of the test device while the electrodes of both are exposed to the solution and their temperature compensation resistors are at the same temperature. Possible damage is avoided because the components do not have to be removed from the monitoring device. If the reading of the voltmeter does not change significantly, substituted components are considered to meet specifications.

In a preferred embodiment, the test unit is provided with a power supply that can be plugged into a service outlet and a shielded housing containing circuits for making necessary interconnections between cables for electrodes and a cable for the preamplifier, the power supply and the voltmeter. Also included therein is a thermal compensation resistor and a switch for coupling it or a thermal compensation resistor of a monitoring device to the preamplifier.

In accordance with another aspect of this invention, all of the components of a monitoring device can be substituted for the components of a test device. A cable is provided that carries operating potentials provided by the power supply to the preamplifier and conducts its output voltage to a terminal that is connected to the voltmeter. The cable is terminated in a plug that fits pins on the amplifier. By coupling this plug to the corresponding pins on the preamplifier of a monitoring device, that preamplifier receives operating potential, and its output voltage is supplied to the voltmeter of the test unit.

In order to reduce the likelihood of false operation, the application of voltages for testing a preamplifier and the substitution of the temperature compensating resistor of a monitoring device for that of the test unit are effected by spring-biased switches.

The test unit could be powered by batteries, but it is preferable that it have a power supply that is adapted to be plugged into the power service system of the plant in order to make it less likely that the test unit will suffer damage by being used in the corrosive atmosphere in the vicinity of a coating machine.

BRIEF DESCRIPTION OF THE DRAWINGS

A detailed discussion of various embodiments of the invention is given below with reference to the following figures, in which like items are identified by the same reference designation, wherein.

DETAILED DESCRIPTION OF THE INVENTION

Figures 1, 1A:
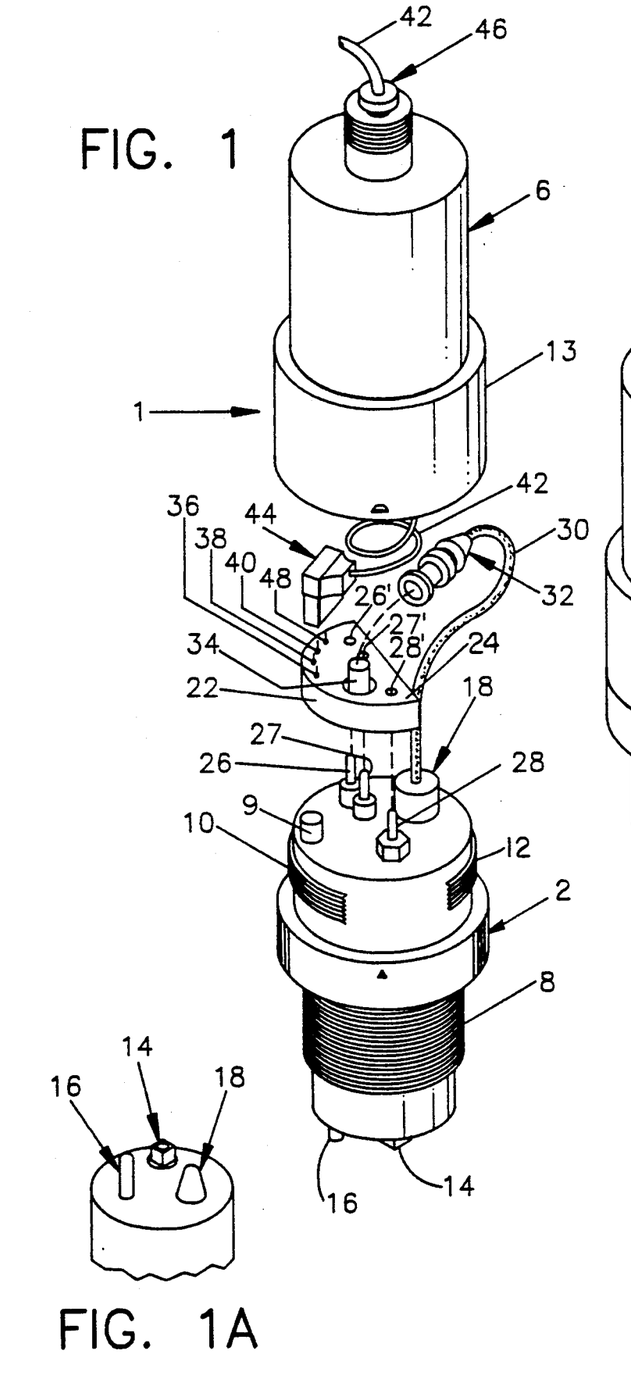
FIG. 1 is an exploded view of one type of monitoring device with which the test unit of this invention may be used.
FIG. 1A is a view of the bottom of the monitoring device of FIG. 1.

In the exploded view of FIG. 1, a monitoring device 1 is shown to be comprised of an electrode body housing 2 and a cover 6. Threads 8 at the bottom of the electrode body housing 2 are adapted to engage internal threads, not shown, in a process tank pipe connection, and circumferentially spaced threads 10 and 12 at the top of the body housing 2 are adapted to engage internal threads, not shown, in the bottom 13 of the cover 6. A wooden junction 14 for a reference electrode and a thimble 16 that contains a thermal compensation resistor project from the bottom of the electrode body housing 2. They are better seen in the bottom view of the housing shown in FIG. 1A, which also shows a tip of a measuring electrode 18.

A preamplifier 22 is mounted on the top of the electrode body housing 2 by insertion of banana plugs 26, 27 and 28 into holes 26', 27' and 28' therein. The plugs 26 and 27 are connected to opposite ends of a thermal compensation resistor, not shown, that is contained in the thimble 16, and the plug 28 is connected to the reference electrode 14. A cable 30 and a BNC connector 32 are provided for connecting the measuring electrode 18, which projects from the surface 24, to an input BNC coupling 34 of the preamplifier 22. Also, a standoff or post 9 is located on the top of housing 2, for spacing the bottom of preamplifier 22 from the top 24.

Operating voltages and a reference potential are respectively supplied to pins 36, 38 and 40 that project from the top 24 of the preamplifier 22 via a cable 42 and a plug 44. The cable 42 passes through the interior of the cover 6 and a cable grip 46. Output voltage from the preamplifier 22 appears on a pin 48 that engages the plug 44 so as to be conveyed via a conductor, not shown, in the cable 42.

Figure 2:
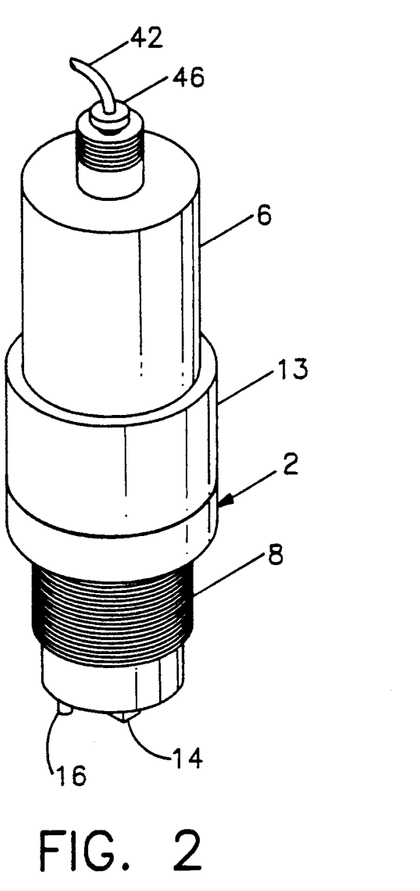
FIG. 2 is an assembled view of the monitoring device of FIG. 1.

When the electrode housing 2, and the cover 6 are assembled, they appear as shown in FIG. 2 in which the wooden junction 14 and the thimble 16 are visible.

Figure 3:
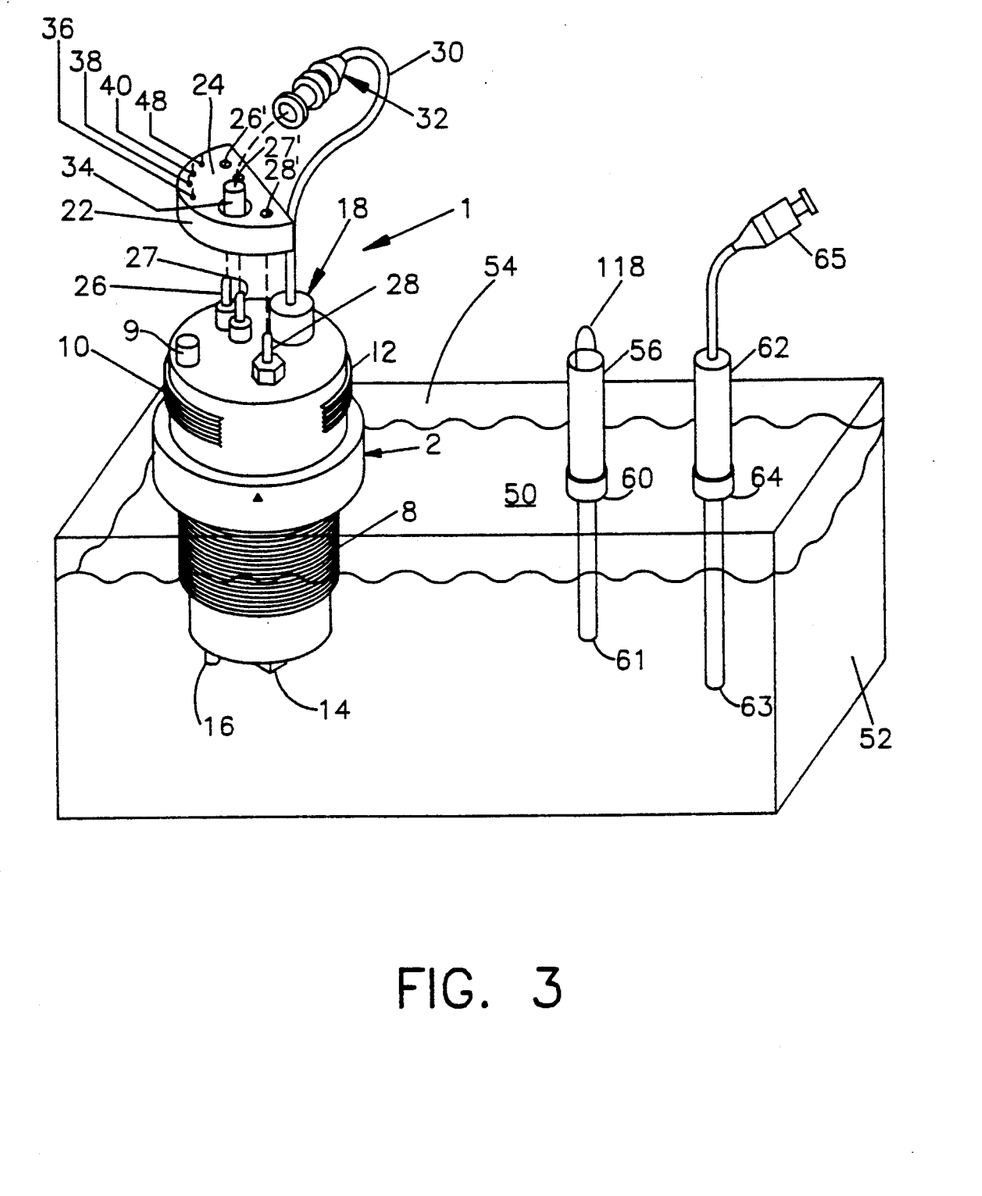
FIG. 3 shows the immersion of a monitoring device and reference and measuring electrodes of a test unit in a standard solution.
Figure 4:
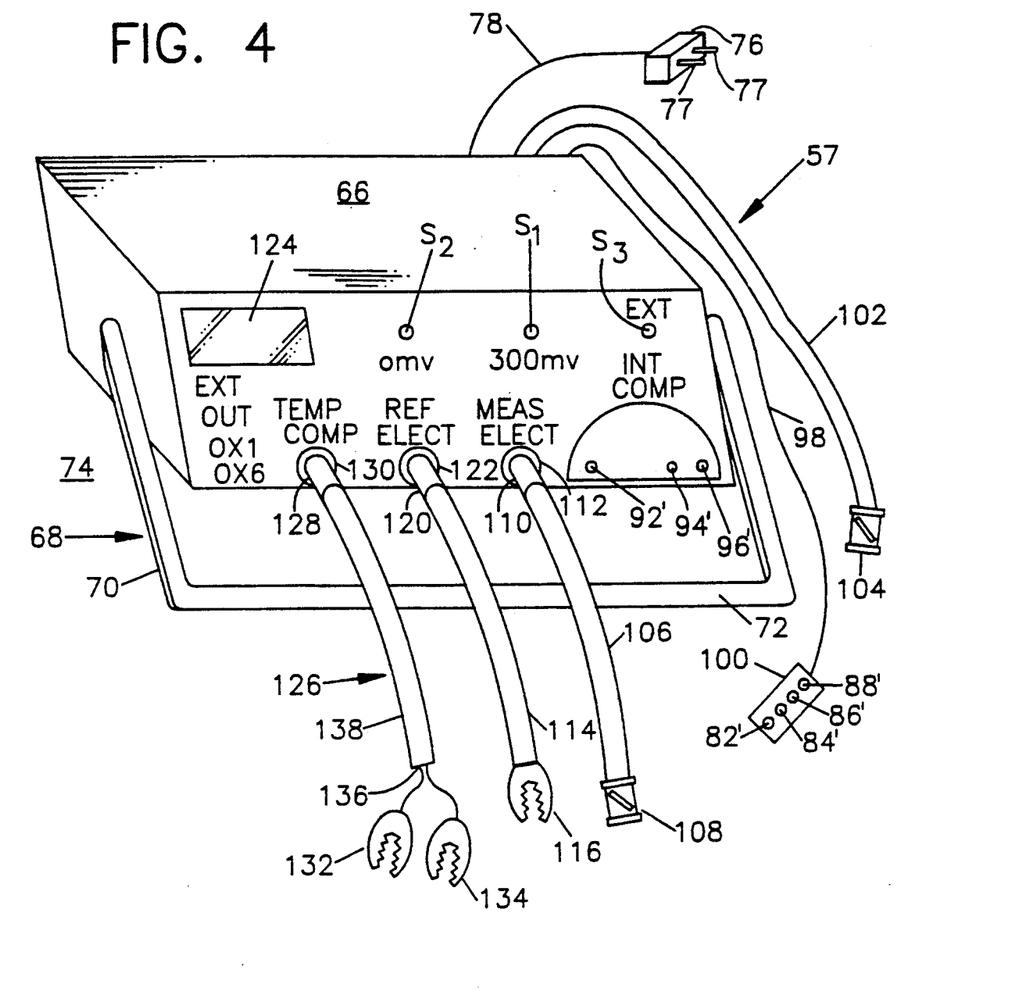
FIG. 4 is an external view of a test unit of this invention showing the cables coupled thereto as well as connections for coupling to an external voltmeter and controls.

In FIG. 3 the monitoring device 1 of FIG. 1 is shown with its cover 6 removed and its electrode housing 2 immersed in a standard solution 50 within a container 52. Although not seen in this view, the portion of body housing 2 which has the largest diameter, rests on the edge of an opening in a cover 54 of the container 52. The container 52 may be of any shape which will minimize the total volume of solution contained therein, while maintaining contact between the bottom of electrodes 14, 16, 61, and 63 which are being utilized in any circuit tests. A reference electrode 56 for test unit 57 of FIG. 4 is mounted at 60 on the edge of an opening not shown, so that the wooden junction 61 thereof extends into the standard solution 50. A measuring electrode 62 for the test unit 57 is mounted at 64 on the edge of an opening, not shown, so that its tip 63 extends into the standard solution 50. A BNC coupling 65 like the BNC coupling 32 is connected to the measurement electrode 62.

Figure 4A:
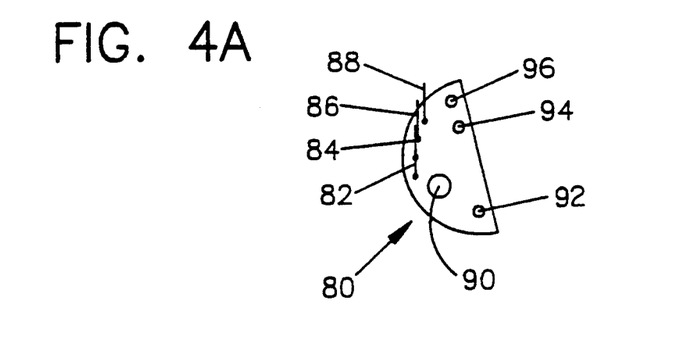
FIG. 4A illustrates the circuit pin and socket connections of a preamplifier for the test unit.
Figure 5A:
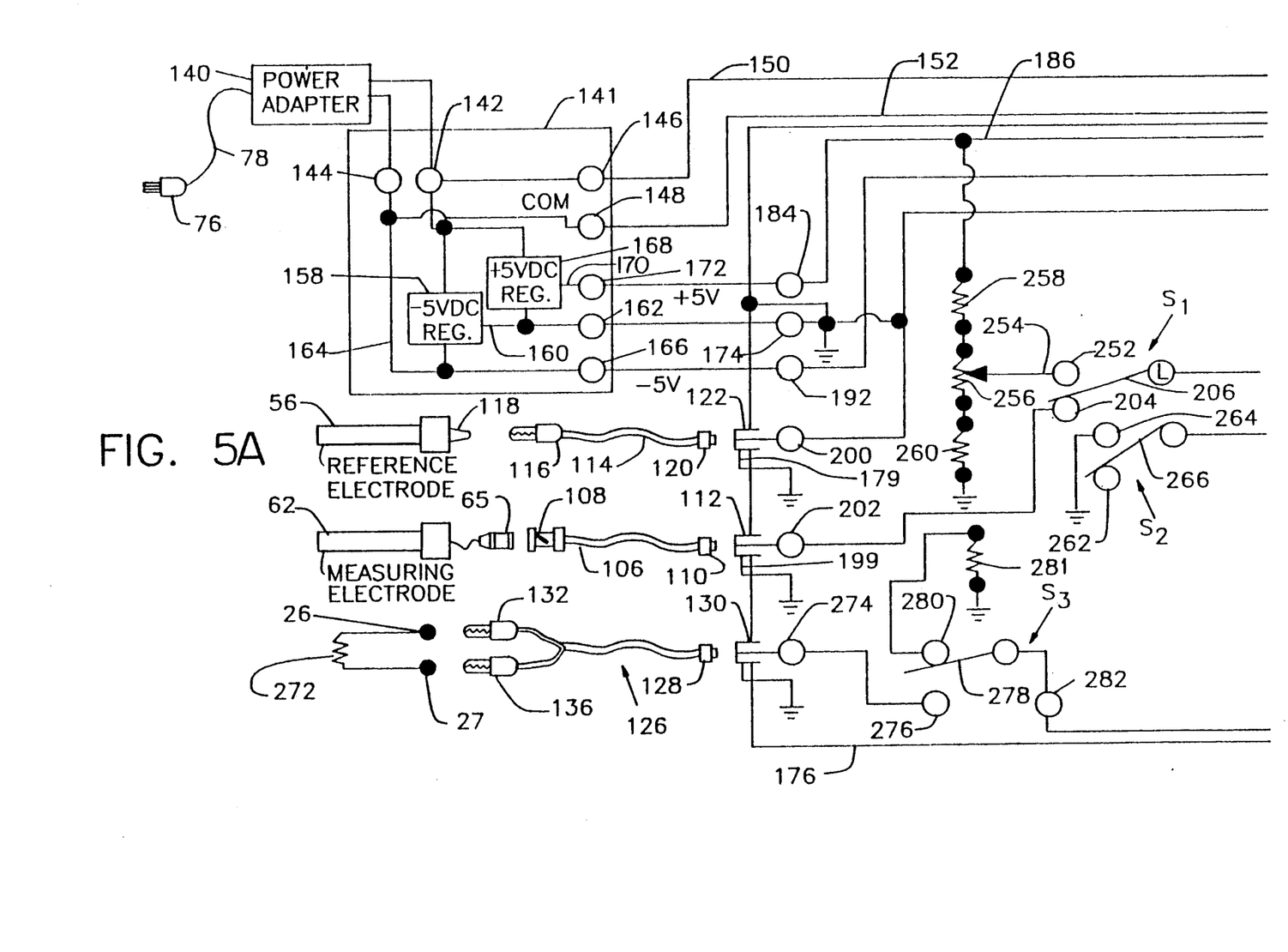
FIG. 5a and 5b is a partial pictorial and partial circuit schematic diagram of a test unit incorporating this invention.
Figure 5B:
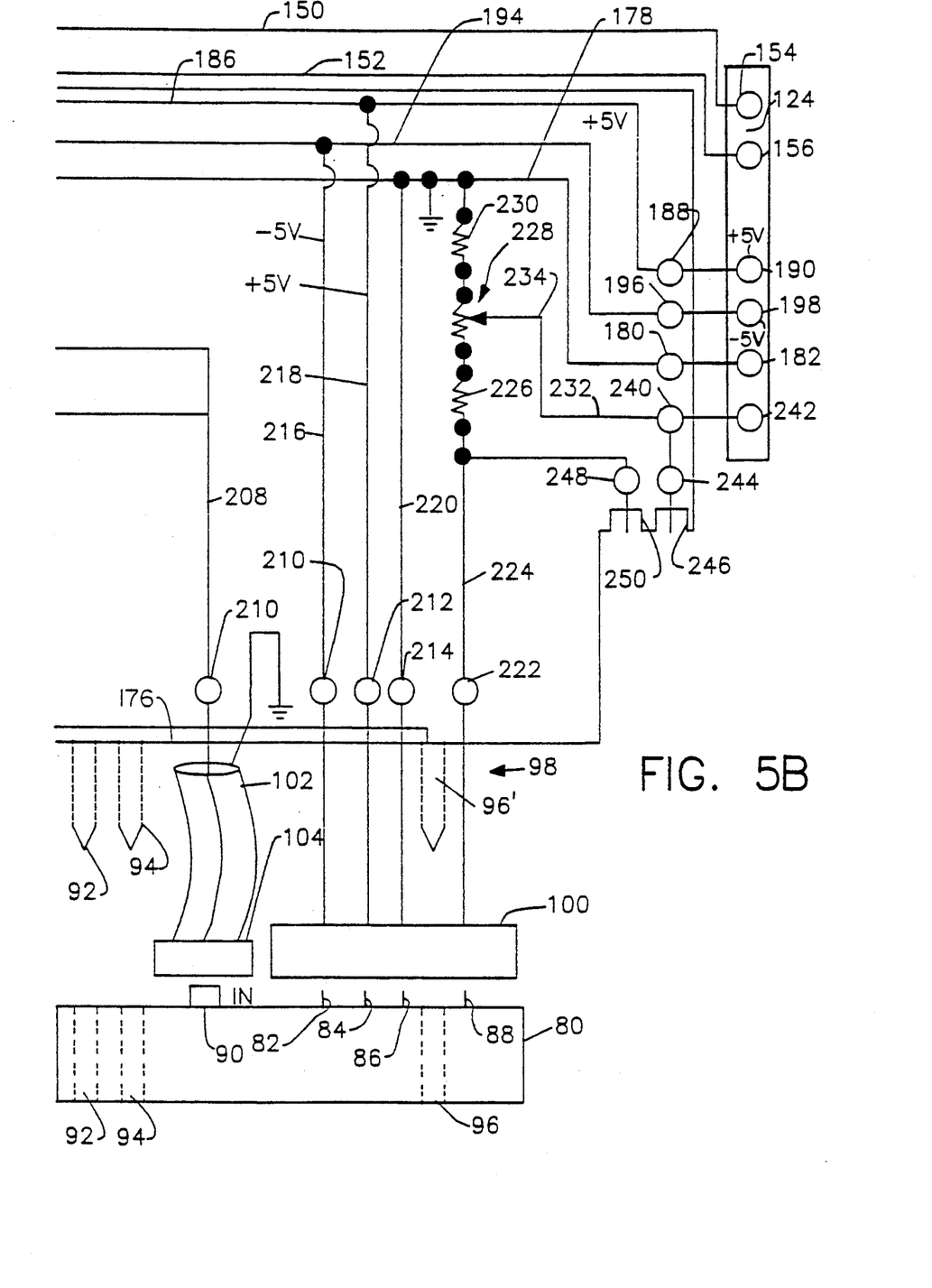

As shown in FIG. 4, the test unit 57 also includes a preamplifier 80 of FIG. 4A that is identical to the preamplifier 22 of FIGS. 1 and 3, a housing 66 for the circuits and voltmeter shown in FIG. 5 and various cables coupled to or passing into the housing 66. The housing 66 is conductive so as to electrically shield the components within it and has a handle 68 with arms 70 and 72 that are respectively rotatably attached to opposite side walls of the housing 66 via detent mechanisms so that the handle can be swung downwardly to adjust the tilt of the housing 66 when it is mounted on a surface 74.

Electrical power for the unit is supplied via a DC power supply module 76 containing a plug 77 that can be inserted into a service outlet and a cord 78. As shown in FIG. 4A, the test unit is provided with a preamplifier 80 that is identical to the preamplifier 22 of FIGS. 1 and 3. It has pins 82, 84, 86 and 88 projecting from one side thereof that, as shown in FIG. 5 to be described, are for application of operating potentials and for providing the output of the preamplifier 80. Also included is a BNC coupling 90 by which input signals are conducted to the preamplifier 80. Apertures 92, 94 and 96 are provided for receiving banana pins 92', 94' and 96' respectively that extend from the housing 66. As will be described in connection with on FIG. 5, the pins 92' and 94' are connected to the housing 66. When the preamplifier 80 is mounted on the housing 66 with the banana pins 92', 94' and 96' respectively extending into the apertures 92, 94 and 96, the pins 82, 84, 86 and 88 extend outwardly as does the BNC coupling 90. A cable 98 from the interior of the housing 66 has a plug 100 at its end provided with female connections 82', 84', 86' and 88' for attachment to the pins 82, 84, 86 and 88 respectively. As previously stated, this provides operating potentials to the preamplifier 80 and conducts its output voltage to the circuits within the housing 66. A cable 102 from the interior of the housing 66 is provided with a BNC coupling 104 at its outer end that can be coupled to the BNC coupling 90 so as to provide input signals to the preamplifier 80.

The measuring electrode 62 of FIG. 3 may be coupled to the circuits in the housing 66 by a coaxial cable 106 having a BNC coupling 108 at one end for connection to the BNC coupling 65 and a male phonojack component 110 at its other end for coupling to a complementary female phonojack component 112 in the housing 66. The reference electrode 56 of FIG. 3 may be coupled to circuits in the housing 66 by a coaxial cable 114 having an alligator clip 116 at one end for attachment to a pin 118 that is connected to the reference electrode 56. A male phonojack component 120 at the other end fits into a complementary female phonojack component 122 in the housing 66. Since, as will be seen in FIG. 5, the circuits of the test unit 57 include their own temperature compensation resistor, no connection need be made to an external resistor when the unit is operating by itself. But when the thermal compensation resistor of the monitoring device 1 is to be checked, a coaxial cable 126 is coupled to the circuit in the housing 66 via a male phonojack portion 128 that mates with a female portion 130. Alligator clips 132 and 134 for connection to the banana pins 26 and 27 of the monitoring device 1 of FIG. 1 are respectively connected to the center conductor 136 and shield 138 of the cable 126. Although the cables 106, 114 and 126 may be coupled to the circuits in the housing 66 in any desired manner, detachable coupling such as the phonojacks are more convenient. It is important, however, that the other ends of the cables be adapted for coupling to the electrodes and the temperature compensation resistor of both the monitoring device and the test unit. If need be, adapters may be used.

In operation of the test unit by itself, voltage built up between the measurement electrode 62 and the reference electrode 56 is applied via the cables 106 and 114 and the circuits in the housing 66 to the cable 102 and via the coupling 90 to the preamplifier 80. The output of the amplifier 80 is conducted to the circuits in the housing 66 via the pin 88 and the female receptor 88' of the plug 100. A voltmeter 124 indicates the value of this output voltage in millivolts, in this example.

In order to check the entire monitoring device 1 with its preamplifier 22 mounted by the banana pins 26, 27 and 28 being inserted in the apertures 26', 27' and 28' and with the BNC connector 32 coupled to the BNC connector 34, it is only necessary to plug in the plug 76 to provide power and couple the female receptors 82', 84', 86' and 88' of the plug 100 of FIG. 3 so that they receive the pins 36, 38, 40 and 48 of the preamplifier 22. None of the cables 102, 106, 114 and 126 are coupled to anything, and it is not necessary to plug in the preamplifier 80.

Checking just the measurement electrode 18 of the monitoring device 1 is accomplished by using the known good preamplifier 80 which is plugged into the front of the test unit 57, where cable 102 is connected to BNC receptacle 90 using BNC plug 104, and cable 98 is connected to the matching pins on preamplifier 80 using plug 100. The BNC coupling 108 of the test unit 57 that is shown in FIG. 4 is connected to the BNC coupling 32 of FIG. 3 and the alligator clip 116 at the end of the cable 114 in FIG. 4 is connected to the pin 118 on the reference electrode 56 in the solution container 52. Thus, the measurement electrode of the monitoring device 1 and the reference electrode of the test unit container 52 provide the input voltage for the preamplifier 80 of the test unit 57. The fact that the tip of the measurement electrode 18 shown on FIG. 1A, which extends from the bottom of the electrode is at a distance from the reference electrode tip 61, makes no significant difference.

Checking just the reference electrode 14 of the monitoring device 1 is accomplished by attaching the alligator clip 116 of the test unit 57 to the reference electrode 28 and attaching the BNC connector 108 of the test unit 57 to the BNC connector 65 for the measuring electrode 62 of the test unit 57. Once again, the fact that there is considerable distance between the electrodes 28 and 62 has no effect.

In checking the electrodes, the standard solution 50 in the container 52 could have any ion concentration because it is only necessary to determine whether an electrode being checked produces the same voltage on the voltmeter 124 as the standard unit it replaces, but it is preferable for the standard solution to have a similar pH and specific ion concentration as the solution in the industrial process in which the monitoring device is immersed, so that the electrodes are tested in a chemical environment similar to that in which they are being used in the chemical process. This avoids introducing chemical changes at the sensitive measuring surfaces which may prevent rapid equilibrium being achieved, absent of unintended chemical reactions or neutralization effects. For example, a commercial pH buffer solution with a pH of 4 is the preferred pH reference solution for pH electrodes being used in a process operating at a pH near 4. A selection of several standard solutions may be used if the intent is to test the response of the electrodes at several different pH and/or specific ion concentrations.

The temperature compensating resistor, not shown, which is inside the thimble 16 of the monitoring device 1 of FIG. 3 is checked by connecting the alligator clips 132 and 136 of the cable 126 to the banana pins 26 and 27 of the monitoring device 1 of FIG. 4 and pushing a spring loaded button 53 that switches the resistor of the monitoring device 1 into the circuit within the housing 56 in a manner to be explained in connection with FIG. 5. For this test, the test device 57 is connected in the same way as when it is operating by itself. This was previously explained.

The preamplifier 22 of the monitoring device 1 is checked b removing it and substituting it for the preamplifier 80 of the test unit by inserting the banana pins 92', 94' and 96' into its apertures 28', 27' and 26' respectively. Two different preset input voltages can be injected by first pushing spring loaded button S2 that shorts the input of the preamplifier 22 to produce a zero millivolt input, then by pushing spring loaded button S1 that injects a voltage produced at wiper 254 in the voltage divider network consisting of resistors 258, 256, and 260, in this example. The voltage reading displayed on voltmeter 124 should be approximately the same as the value printed above the respective spring loaded button switches S2 and S1 when each is pushed.

Reference is now made to FIG. 5 for a description of the circuits that are enclosed within the housing 66. Those components that appear in other drawings are designated by the same numbers.

The service plug 76 is coupled via the cord 78 to an unregulated D.C. voltage supply 140 that is coupled to terminals 142 and 144 of a regulated D.C. voltage supply 141 in such manner that the terminal 142 is in this particular embodiment 12 volts positive with respect to the terminal 144. The terminals 142 and 144 are respectively coupled via terminals 146 and 148 and conductors 150 and 152 to terminals 154 and 156 of the voltmeter 124 so as to provide it with voltage for running a backlight.

A regulated voltage supply 158 is coupled between the terminals 142 and 144 so as to produce a voltage on its output lead 160 and a terminal 162 to which the lead 160 is connected that is +5 volts with respect to the terminal 144. The terminal 144 is connected by a conductor 164 to a terminal 166. A regulated power supply 168 is connected between the terminal 142 and the lead 160 so as to establish its output lead 170 and a terminal 172 to which it is connected at a voltage that is +5 volts with respect to the lead 160. The terminal 162 is connected to an input terminal 174 that is connected to a housing 176 that serves as a floating ground. Thus, the voltage at the terminal 172 of the power supply is +5 volts with respect to the terminal 162, and the voltage at the terminal 166 of the power supply is −5 volts with respect to the terminal 162.

Operating voltages for the voltmeter 124 are provided in the following manner. A conductor 178 is connected between the floating ground input terminal 174 and an output terminal 180, which is connected to an input terminal 182 of the voltmeter 124. A voltage that is +5 volts with respect to floating ground is supplied via a connection between the terminal 172 and an input terminal 184, a conductor 186 between the terminal 184 and an output terminal 188 and a connection between the terminal 188 and an input terminal 190 of the voltmeter 124, in this example. A voltage that is −5 volts with respect to floating ground is supplied via a connection between the terminal 166 of the power supply 141 and an input terminal 192, a conductor 194 between the terminal 192 and an output terminal 196 and a connection between the terminal 196 and an input terminal 198 of the voltmeter 124. The variety of panel meters commercially available are such that different methods of powering the meter than that shown here may be required, depending upon the specific panel meter chosen to be used.

The manner in which reference and measuring electrodes are coupled to a preamplifier such as 80 is now explained. Assume that the reference electrode used is the electrode 56 of the test unit 57. As explained in connection with FIG. 4, it is coupled via a pin 118, a clip 116 and a coaxial cable 114 to a phonojack 120, 122. The central conductor of the cable 114 to which the electrode 56 is connected to an input terminal 200 that is connected to the grounded conductor 178. The shield of the cable 114 is also connected to floating ground as indicated at 179 when the phonojack 120, 122 is coupled.

Assume that the measuring electrode used is the electrode 62 of the test unit 57. As explained in connection with FIG. 4, it is coupled via a BNC connector 65, a BNC connector 108, a coaxial cable 106 to a phonojack 110, 112. The shield of the cable 106 is connected to floating ground, as indicated at 199, and its center conductor is connected to an input terminal 202. The terminal 202 is connected to a terminal 204 of a switch S that has its arm 206 spring biased, as indicated by the arrow into contact with the terminal 204. The arm 206 is connected via a conductor 208 to a terminal 210 and a center conductor of the coaxial cable 102 that is coupled by the BNC connector 104 to the input 90 of the preamplifier 80.

Operating voltages for the preamplifier 80 are respectively provided via the pins 82, 84, and 86 extending from the preamplifier 80, the plug 100 into which they fit, the terminals 210, 212 and 214, and the conductors 216, 218 and 220 that are respectively connected to the conductor 194 that is at −5 volts, the conductor 186 that is at +5 volts and the conductor 178 that is connected to floating ground.

The output voltage of the preamplifier 80 appears at the pin 88, which is connected via the plug 100, a terminal 222, a conductor 224, a series circuit comprised of a resistor 226, a potentiometer 228 and a resistor 230 to the conductor 178 that is at ground potential. A conductor 232 is connected between the movable arm 234 of the potentiometer 228 to a terminal 240 that is connected to a voltage input terminal 242 of the voltmeter 124.

In order to make it possible for the voltage at the terminal 240 to be indicated on a voltmeter external to the test unit, a terminal 244 is connected between the terminal 240 and a phonojack 246, and in order for the full output voltage of the preamplifier 80 to be indicated in an external voltmeter, a terminal 248 is connected between a phonojack 250 and the conductor 224.

The gain of the preamplifier in this particular embodiment of the invention is approximately six, and the potentiometer 228 is adjusted so as to apply one-sixth of the output voltage of a preamplifier such as 80 to the input terminal 242 of the voltmeter 124. Thus the overall gain between the preamplifier 80 input and the voltmeter display 124 is unity. This is done so that the voltage indicated by the voltmeter 124 will be the same as that produced by the electrode pair 56, 62 in a standard solution. Although not necessary, having only one voltage to consider lessens the confusion.

In order to check the gain of the preamplifier 80, another terminal 252 of the switch $S_1$ is connected to the arm 254 of a potentiometer 256. The potentiometer 256 is connected in series with resistors 258 and 260 on either side of it between floating ground and the conductor 186 that is at +5 volts. As previously stated, the arm 206 is spring biased into contact with the terminal 204. The potentiometer 256 is adjusted with the aid of other instruments so that it produces a known voltage so that if the preamplifier 80 has a gain of 6, as required and potentiometer 228 is properly adjusted, the voltage indicated will be the same as the input voltage to the preamplifier 80. A check is also made at the low end of the range by provision of a switch $S_2$ having an unconnected terminal 262, a grounded terminal 264 and an arm 266 that is connected to the conductor 208 and is spring biased into contact with the unconnected terminal 262.

Checking a temperature compensation resistor 272 is accomplished by coupling it to the phonojack 128, 130 by the coaxial cable 126 so that one side of the resistor 272 is at floating ground. The other side of the resistor is connected to a terminal 274 that is in turn connected to a terminal 276 of a switch $S_3$ that is also shown in FIG. 4 $S_3$ has an arm 278 that is spring biased into contact with another terminal 280. A standard resistor 281 (having at room temperature a resistance substantially equal to that of temperature compensation resistor 272, which is about 3KΩ in this example at room temperature) is connected between the terminal 280 and floating ground. The arm 278 is connected to a terminal 282 that is connected to a banana pin 96′, and banana pins 92′ and 94′ are connected to floating ground. The pins respectively fit into apertures 92′, 94′ and 96′ of the preamplifier 80 so as to support it. The aperture 96′ is connected to an appropriate point in the circuit of the preamplifier 80. Thus, the thermal compensation resistor 272 is tested relative to standard resistor 281 at room temperature, in this example. After the temperature of the resistor 272 of the monitoring device 1 has had time to reach the ambient laboratory temperature, the switch $S_3$ is activated so as to substitute the thermal compensation resistor 272 of the monitoring device for the resistor 281 in the test unit 57. If the voltage indicated by the voltmeter 124 does not change significantly, the resistor 272 is considered to meet specifications.

The preamplifier 22 of the monitoring device 1 can be checked by substituting it for the preamplifier 80 of the test unit which has been checked as previously explained. Any combination of reference and measuring electrodes that are known to meet specifications by tests previously described may be used, but it would be preferable to use the electrodes 56 and 62 of the test unit.

Although various embodiments of the invention have been shown and described herein, they are not meant to be limiting. Those of skill in the art may recognize various modifications to the embodiments, which modifications are meant to be covered by the spirit and scope of the appended claims.

What is claimed is:

1. A test unit for a monitoring device, said monitoring device having a reference electrode, a measuring electrode, and a preamplifier having an input coupled to said electrodes and an output; said test unit comprising:
   a reference electrode;
   a measuring electrode;
   a preamplifier having an input means and an output;
   a first cable having one end coupled to said input means and its other end adapted for connection to the reference electrode of said monitoring device or to the reference electrode of said test unit;

a second cable having one end coupled to said input means and its other end adapted for connection to the measuring electrode of said monitoring device or the measuring electrode of said test unit;

a voltmeter;

means for coupling the output of said preamplifier of said test unit to said voltmeter;

a power supply for providing operating potentials to said preamplifier of said test unit; and means for coupling the operating potentials produced by said power supply to the preamplifier of said test unit.

2. A test unit as set forth in claim 1 wherein said means for coupling said output of the preamplifier of said test unit to said voltmeter and the operating potentials from said power supply to said preamplifier of said test unit includes connection via a cable terminating in a plug adapted for coupling to the preamplifier of said monitoring device or the preamplifier of the test unit.

3. A test unit as set forth in claim 2 for a monitoring device having a temperature compensation resistor, the test unit further comprising:

a switch having first and second terminals and an output;

a thermal compensation resistor connected to said first terminal;

a third cable adapted for connecting the temperature compensation resistor of said monitoring device to said second terminal; and means coupling the output of said switch to the preamplifier of the test unit.

4. A test unit for a monitoring device, said monitoring device having a preamplifier with reference and measuring electrodes coupled to an input thereof, first connectors for application of operating potentials and a second connector at which its output voltage appears, said test unit comprising:

a power supply;

a voltmeter having an input;

a plug having third connectors adapted to mate with said first connectors of the preamplifier of said monitoring device;

a plurality of conductors respectively connected between said power supply and said third connectors in said plug;

said plug having a fourth connector adapted to mate with said second connector of said preamplifier of said monitoring device; and a conductor connected between the input of said voltmeter and the fourth connector in said plug; whereby, the entire monitoring device is checked by mating the third connectors of said plug with said first connectors of said monitoring device and the fourth connector of said plug with the second connector.

5. A test unit as set forth in claim 4 further comprising:

means for checking a temperature compensation resistor for the preamplifier of said monitoring device, said means comprising:

a preamplifier having input means for coupling reference and measuring electrodes;

a reference electrode coupled to one input means;

a measuring electrode coupled to the other input means;

a power supply coupled to said last mentioned preamplifier;

a temperature compensation resistor;

a cable having one end adapted for coupling to the thermal compensation resistor of said monitoring device; and means for connecting either of said temperature compensation resistor or said cable to said last mentioned preamplifier.

6. A test unit as set forth in claim 4 further including means for separately and jointly checking the reference and measuring electrodes of said monitoring device, said last mentioned means comprising:

a preamplifier;

a reference electrode;

a measuring electrode;

a first cable having one end adapted for coupling to one input coupling means of said last mentioned preamplifier and means at its other end adapted for detachable connection to said reference electrode of said monitoring device or to said reference electrode of said test unit; and a second cable having one end adapted for coupling to the other input coupling means of said last mentioned preamplifier and means at its other end adapted for detachable connection to said measuring electrode of said monitoring device or to said measuring electrode of said test unit.

7. A test unit as set forth in claim 6 further comprising:

a container;

a standard solution in said container;

said container having means for mounting said monitoring device so that its reference and measuring electrodes are immersed in said solution;

means for mounting the reference electrode of said test unit so that it is immersed in said solution; and means for mounting the measuring electrode of said test unit so that it is immersed in said solution.

8. A test unit comprising:

a preamplifier having an input for voltage to be amplified, an output for amplified voltage and means for application of operating potential;

a reference electrode;

a measuring electrode;

a source of reference potential;

a first cable having one end coupled to said source of reference potential, and another end adapted for detachable coupling to said reference electrode;

a second cable having one end coupled to said input, and another end adapted for detachable coupling to said measuring electrode;

a power supply;

means for coupling said power supply to said means for application of operating potential;

a voltmeter;

means for coupling said voltmeter to said output of said preamplifier;

means for providing a test voltage; and switching means for selectively coupling said test voltage or one of said first and second cables to said input of said preamplifier that is for voltages to be amplified, whereby the voltage gain of said amplifier can be checked.

9. A test unit comprising: a preamplifier having an input for voltage to be amplified, an output for amplified voltage and means for application of operating potential;

a reference electrode;

a measuring electrode;

a source of reference potential;

a first cable having one end coupled to said source of reference potential, and another end adapted for detachable coupling to said reference electrode;

a second cable having one end coupled to said input, and another end adapted for detachable coupling to said measuring electrode;

a power supply;

means for coupling said power supply to said means for application of operating potential;

a voltmeter;

means for coupling said voltmeter to said output of said preamplifier;

connection means in said preamplifier for a thermal compensation resistor;

a thermal compensation resistor;

a third cable; and switching means for selectively coupling said thermal compensation resistor or said third cable to said connection means of said preamplifier.

10. A test unit as set forth in claim 9 further comprising:

means for providing a test voltage; and switching means for selectively coupling said test voltage or one of said first and second cables to said input of said preamplifier that is for voltages to be amplified, whereby the voltage gain of said preamplifier can be checked.

11. A test unit for a monitoring device having a reference electrode, a measuring electrode and a preamplifier having an input coupled to said electrodes and an output; said test unit comprising:

a housing of conductive material;

first terminals mounted on said housing adapted to be attached to a D.C. power supply;

first connectors mounted on said housing;

conductors within said housing for respectively connecting said first terminals and said first connectors;

another terminal mounted on said housing;

a voltmeter coupled to said another terminal;

another connector mounted on said housing;

means within said housing for respectively connecting said another terminal to said another connector;

a first and second coaxial cable couplings mounted on said housing so that the shield of coaxial cables respectively coupled thereto are connected to said housing;

a first conductor within said housing connected between said first and second coaxial cable couplings so as to connect the center conductors of coaxial cables respectively coupled thereto;

a third coaxial cable coupling mounted on said housing so that the shield of a coaxial cable coupled thereto is connected to said housing;

means coupled to said third coaxial coupling for connecting the center conductor of a coaxial cable coupled thereto to said housing;

a preamplifier having third connectors for the application of operating potentials;

an additional connector at which its output voltage appears, and a third coaxial cable coupling;

a cable having means at one end for respectively connecting conductors therein to said first connectors and said another connector and a plug at its other end, said plug being adapted for coupling to s id third connectors and said additional connector of said preamplifier; and a coaxial cable coupled between said second coaxial cable coupling on said housing and said coaxial cable coupling of said preamplifier.

12. A test unit as set forth in claim 11 further comprising:

means within said housing for driving from a voltage applied to one of said first terminals a test voltage; and switching means for applying said test voltage or the voltage on said first conductor to the center conductor of said third coaxial cable.

13. A test unit as set forth in claim 11 further comprising:

a measuring electrode; and a coaxial cable for coupling said measuring electrode to said first coaxial cable coupling on said housing.

14. A test unit a set forth in claim 13 further comprising:

a reference electrode; and a coaxial cable for coupling said reference electrode to said third coaxial cable coupling.

15. A test unit as set forth in claim 11 further comprising:

first coupling means on said preamplifier to which a thermal compensation resistor is to be connected;

an internal thermal compensation resistor within said housing;

second coupling means on said housing adapted for the coupling of opposite ends of an external temperature compensation resistor; and switching means for selectively coupling either said internal temperature compensation resistor or said second coupling means to said first coupling means on said preamplifier.

16. A test unit as set forth in claim 15 further comprising a cable having means at one end for coupling to opposite sides of a thermal compensation resistor and conductors therein for connection to said second coupling means.

17. A test unit as set forth in claim 15 further comprising:

a coaxial cable for coupling said measuring electrode to said first coaxial cable coupling on said housing;

a reference electrode;

a coaxial cable for coupling said reference electrode to said third coaxial cable coupling;

a cable having means at one end for coupling to opposite sides of a thermal compensation resistor and conductors therein for connection to said second coupling means;

a container having a test solution therein; and means for mounting a monitoring device so that its reference and measuring electrodes are exposed to said solution.

18. A test unit as set forth in claim 14 further comprising:

a container having a test solution therein;

means for mounting said reference and measuring electrodes so that they are exposed to said solution.

19. A test unit as set forth in claim 18 further comprising:

means for mounting a monitoring device so that its reference and measuring electrodes are exposed to said solution.

* * * * *